United States Patent [19]

Kimble et al.

[11] Patent Number: 4,533,467
[45] Date of Patent: Aug. 6, 1985

[54] ORE FLOTATION AND FLOTATION AGENTS FOR USE THEREIN

[75] Inventors: Kenneth B. Kimble; Clarence R. Bresson; Harold W. Mark, all of Bartlesville, Okla.

[73] Assignee: Phillips Petroleum Company, Bartlesville, Okla.

[21] Appl. No.: 608,827

[22] Filed: May 10, 1984

[51] Int. Cl.$^3$ .................... B03D 1/02; C07C 153/00; C22B 3/00
[52] U.S. Cl. .................... 209/167; 209/166; 252/61; 260/455 B
[58] Field of Search .................. 252/61; 209/166, 167; 260/455 B

[56] References Cited

U.S. PATENT DOCUMENTS

| | | | |
|---|---|---|---|
| 2,197,964 | 4/1940 | Bishop | 260/455 B |
| 2,600,624 | 6/1952 | Del Zoppo | 260/455 B |
| 3,660,412 | 5/1972 | Haugwitz | 260/455 B |

*Primary Examiner*—Paul Lieberman
*Assistant Examiner*—Robert A. Wax
*Attorney, Agent, or Firm*—French and Doescher

[57] ABSTRACT

Diammonium bis(carboxyalkyl)-trithiocarbonate salts, dialkali metal bis(carboxyalkyl)-trithiocarbonate salts, their use as flotation agents, and a process for the production of these novel compositions are disclosed.

22 Claims, No Drawings

ORE FLOTATION AND FLOTATION AGENTS FOR USE THEREIN

This invention relates generally to novel chemical compositions. In one aspect, the invention relates to a process for making such compositions. In another aspect, the invention relates to ore flotation processes employing such novel compositions.

Froth flotation is a process for recovering and concentrating minerals from ores. In a froth flotation process, the ore is crushed and wet ground to obtain a pulp. Additives such as mineral flotation or collecting agents, frothing agents, suppressants, stabilizers, etc. are added to the pulp to assist separating valuable minerals from the undesired or gangue portions of the ore in subsequent flotation steps. The pulp is then aerated to produce a froth at the surface. The minerals which adhere to the bubbles or froth are skimmed or otherwise removed and separated. Selective suppressants or depressants inhibit the adherence of certain minerals to the bubbles or froth thus assisting in the separation of the froth product from the reject product which includes those minerals suppressed by the suppressant agent. The froth product or the reject product or both can then be further processed to obtain the desired minerals. Generally the ore is floated to produce a rougher concentrate, the rougher concentrate thereafter being refloated in the presence of suppressants to further separate the minerals therein. Typical mineral flotation collectors include xanthates, amines, alkyl sulfates, arenes, sulfonates, dithiocarbamates, dithiophosphates, and thiols.

It is known from the art that some organic derivatives of trithiocarbonic acid are useful as flotation agents. U.S. Pat. No. 1,659,396, for instance, describes diethyl trithiocarbonate and the production thereof. U.S. Pat. No. 3,166,580 describes dicyclopentyl trithiocarbonates and their production as well as the utility of these compounds as flotation agents.

It is a continuing goal in the ore-processing industry to increase the productivity of ore flotation processes and, above all, to provide specific procedures which are selective to one ore or metal over other ores or metals present in the treated material.

It is an object of the invention to provide a novel composition of matter.

Another object of the invention is to provide new trithiocarbonates.

A further object of the invention is to provide a process for producing such new trithiocarbonates.

Yet another object of the invention is to provide an improved ore flotation process wherein such new trithiocarbonates are used as flotation agents.

Still another object of the invention is to provide a novel suppressant suitable for use in an ore flotation process.

These and other objects, advantages, details, features and embodiments of this invention will become apparent to those skilled in the art from the following detailed description of the invention and the appended claims.

In accordance with this invention it has been found that diammnonium bis(carboxyalkyl)-trithiocarbonate salts and dialkali metal bis(carboxyalkyl)-trithiocarbonate salts are very effective and selective ore flotation agents.

Thus, in accordance with a first aspect of this invention, novel compositions of matter are provided which can be characterized by the formula $$MOOCR^1S-\overset{\overset{S}{\|}}{C}-SR^2COOM,$$

wherein M is selected from the group consisting of ammonium and alkali metals from Group IA of the Periodic Table of the Elements, $R^1$ is selected from the group consisting of alkylene radicals, $R^2$ is selected from the group consisting of alkylene radicals, and $R^1$ and $R^2$ can be the same or different.

In accordance with a second aspect of the invention there is provided a process for producing the above-defined novel trithiocarbonate salts. This process comprises:

(a) reacting a hydroxide having the formula $$MOH \qquad (I),$$

wherein M is selected from the group consisting of ammonium and alkali metals from Group IA of the Periodic Table of Elements, with a mercaptoalkanoic acid having the formula $$HOOCR^1-SH \qquad (II),$$

wherein $R^1$ is selected from the group consisting of alkylene radicals, and with $CS_2$ to form $$MOOCR^1S-\overset{\overset{S}{\|}}{C}-SM; \qquad (III)$$

(b) reacting the product of formula (III) with a haloalkanoic acid having the formula $$X-R^2COOH \qquad (IV),$$

wherein X is selected from the group consisting of Cl, Br and I, and $R^2$ is selected from the group consisting of alkylene radicals, to form a trithiocarbonate having the formula $$MOOCR^1S-\overset{\overset{S}{\|}}{C}-SR^2COOM; \text{ and} \qquad (V)$$

(c) recovering the product of formula (V) as the product of the process.

Exemplary reagents represented by formula (II) above include, but are not limited to
mercaptoacetic acid (thioglycolic acid),
3-mercaptopropionic acid,
2-mercaptopropionic acid (thiolactic acid),
2-mercaptobutanoic acid,
4-mercaptobutanoic acid, and
6-mercaptohexanoic acid.

Exemplary reagents represented by formula (IV) above include, but are not limited to
chloroacetic acid,
bromoacetic acid,
iodoacetic acid,
2-chloropropionic acid,
3-chloropropionic acid,
4-chlorobutanoic acid, and
6-chlorohexanoic acid.

The detailed operating conditions for the individual steps are not critical and specific values for the steps can be seen from the following examples. Generally the first step of the process, namely the reaction of the mercaptoalkanoic acid with the alkali metal hydroxide or ammonium hydroxide and the carbon disulfide, is carried out in an aqueous environment and at a temperature in the range from about 25° C. to about 100° C. and under a pressure of from about 0 to about 500 psig. The reaction time for this first step is somewhat dependent upon the other reaction conditions but will generally be in the range of from about 1 to about 2 hours.

The reaction of the product of formula (III) with the haloalkanoic acid will generally be carried out by a slow addition of the two compounds and mixing. The resulting exothermic reaction is generally maintained at a temperature in the range from about 25° C. to about 100° C. and at a pressure in the range from about 0 to about 500 psig for a time in the range from about 1 to about 10 hours.

The recovery of the product of formula (V) can be carried out by standard techniques.

A further aspect of this invention resides in an ore flotation process. More specifically, such further aspect of this invention resides in a process for separating valuable ore materials from gangue materials. The ore flotation process of this invention distinguishes over the known ore flotation processes primarily in the employment of a new flotation agent to be defined. Otherwise the recovery process involves crushing of the ore and ore grinding to obtain a pulp. In this pulp the flotation agent is incorporated and the pulp is aerated to produce a froth at the surface which is rich in valuable ore materials but depleted of the gangue materials or vice versa. The ore materials, optionally, after additional flotation or frothing steps in which the novel flotation agent can be employed, are recovered. In addition to the novel flotation agent of the present invention, frothing agents, collectors, promoters, depressants and stabilizers which are known in the art can be used in the various steps. Generally the novel suppressant of the present invention will be advantageously employed in the flotation of a rougher concentrate following the use of a collector in a prior flotation step wherein Mo, Cu, Fe, etc. are separated as the rougher concentrate from the gangue materials in the ore.

The trithiocarbonates useful in the ore flotation process of this invention are characterized by the formula

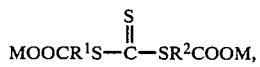

$$MOOCR^1S-\overset{\overset{S}{\|}}{C}-SR^2COOM,$$

wherein M is selected from the group consisting of ammonium and alkali metals from Group IA of the Periodic Table of the Elements, $R^1$ is selected from the group consisting of alkylene radicals, $R^2$ is selected from the group consisting of alkylene radicals, and $R^1$ and $R^2$ can be the same or different.

It is presently preferred that the alkylene radicals of $R^1$ and $R^2$ each have from 1 to 6 carbon atoms. The alkylene radicals of $R^1$ and $R^2$ can be linear or branched. Examples of such compounds useful as flotation agents in the process of this invention are those generally characterized as diammonium bis(carboxyalkyl)-trithiocarbonate and dialkali metal bis(carboxyalkyl)-trithiocarbonate, such as, for example, disodium 2-carboxyethylcarboxymethyl trithiocarbonate,
bis(sodium carboxymethyl)-trithiocarbonate,
bis(sodium 2-carboxyethyl)-trithiocarbonate,
bis(sodium 3-carboxypropyl)-trithiocarbonate,
bis(potassium carboxymethyl)-trithiocarbonate,
bis(lithium carboxymethyl)-trithiocarbonate,
diammonium 2-carboxyethylcarboxymethyl trithiocarbonate,
bis(ammonium carboxymethyl)-trithiocarbonate,
dipotassium 2-carboxyethylcarboxymethyl trithiocarbonate,
and the like, and mixtures of any two or more thereof.

The presently preferred compositions used as the flotation agents in the process of this invention are disodium 2-carboxyethylcarboxymethyl trithiocarbonate and bis(sodium carboxymethyl)trithiocarbonate.

The amount of dialkali metal bis(carboxyalkyl)-trithiocarbonate and/or diammonium bis(carboxyalkyl)-trithiocarbonate employed in the mineral recovery process of this invention is not critical. The quantity will depend upon the process parameters. Generally, the trithiocarbonates of the present invention will be employed in the ore flotation mineral recovery process of the present invention at concentration levels sufficient to provide the desired suppressant (or depressant) action on certain minerals. The amount of dialkali metal bis(carboxyalkyl)-trithiocarbonate and/or diammonium bis(carboxyalkyl)-trithiocarbonate employed as a suppressant in the mineral recovery process of this invention will generally range from about 0.005 lb to about 10 lb of the dialkali metal bis(carboxyalkyl)-trithiocarbonate and/or diammonium bis(carboxyalkyl)-trithiocarbonate per ton of solids or crushed ore, and more preferably range from 0.1 to about 6 lb/ton of solids or crushed ore. The trithiocarbonate suppressants or depressants of the present invention can be added to an ore flotation mineral recovery process or system at the ore-grinding stage, the ore flotation step and/or to the concentrate which is to be further floated.

Various flotation agents or processing aids can be used in conjunction with the novel trithiocarbonate suppressants of the present invention such as, for example, flocculents, frothers, dispersants, promoters and the like.

A surprising characteristic of the novel trithiocarbonate suppressants of the present invention is their ability to function in an ore flotation mineral recovery process over a broad range of pH values. A general range of these pH values extends from around 6.5 to about 10.4 pH.

It is generally believed that the novel trithiocarbonates disclosed herein are useful for separating any valuable metal sulfide from its corresponding gangue material. It is also understood that the novel trithiocarbonates can facilitate the separation of a mixture of metals that are contained in a particular mining deposit or ore, said mixture being further separated by subsequent froth flotations or any other conventional separating methods. The trithiocarbonates herein disclosed are particularly useful as copper and/or iron suppressants in the separation of molybdenum and/or lead minerals from the total ore. Examples of such molybdenum-bearing ores include, but are not limited to such materials as

| Molybdenum-Bearing ores: | |
|---|---|
| Molybdenite | $MoS_2$ |
| Wulfenite | $PbMoO_4$ |
| Powellite | $Ca(Mo, W)O_4$ |

| -continued | |
|---|---|
| Molybdenum-Bearing ores: | |
| Ferrimolybdite | $Fe_2Mo_3O_{12}.8H_2O$ |

Other metal bearing ores within the scope of this invention are, for example, but are not limited to, such materials as

| Copper-bearing ores: | |
|---|---|
| Covellite | CuS |
| Chalcocite | $Cu_2S$ |
| Chalcopyrite | $CuFeS_2$ |
| Bornite | $Cu_5FeS_4$ |
| Cubanite | $Cu_2SFe_4S_5$ |
| Valerite | $Cu_2Fe_4S_7$ or $Cu_3Fe_4S_7$ |
| Enargite | $Cu_3(As, Sb)S_4$ |
| Tetrahedrite | $Cu_3SbS_2$ |
| Tennanite | $Cu_{12}As_4S_{13}$ |
| Cuprite | $Cu_2O$ |
| Tenorite | CuO |
| Malachite | $Cu_2(OH)_2CO_3$ |
| Azurite | $Cu_3(OH)_2CO_3$ |
| Antlerite | $Cu_3SO_4(OH)_4$ |
| Brochantite | $Cu_4(OH)_6SO_4$ |
| Atacamite | $Cu_2Cl(OH)_3$ |
| Chrysocolla | $CuSiO_3$ |
| Famatinite | $Cu_3(Sb, As)S_4$ |
| Bournonite | $PbCuSbS_3$ |
| Lead-Bearing ore: | |
| Galena | PbS |
| Antimony-Bearing ore: | |
| Stibnite | $Sb_2S_3$ |
| Zinc-Bearing ores: | |
| Sphalerite | ZnS |
| Zincite | ZnO |
| Smithsonite | $ZnCO_3$ |
| Chromium-Bearing ores: | |
| Daubreelite | $FeSCrS_3$ |
| Chromite | $FeO.Cr_2O_3$ |
| Iron-Bearing ores: | |
| Pyrite or Marcasite | $FeS_2$ |
| Pyrrhotite | $Fe_5S_6$ to $Fe_{16}S_{17}$ |
| Nickel-Bearing ores: | |
| Pentlandite | (FeNi)S |
| Millerite | NiS |
| Niccolite | NiAs |

The presently preferred ores in connection with which the process of this invention is applied are molybdenum, lead, copper and iron ores or minerals.

SEPARATION CONDITIONS

Any froth flotation apparatus can be used in this invention. The most commonly used commercial flotation machines are the Agitar (Galigher Co.), Denver Sub-A (Denver Equipment Co.), and the Fagergren (Western Machinery Co.). Smaller laboratory scale apparatus such as the Hallimond cell can also be used.

The instant invention was demonstrated in tests conducted at ambient room temperature to about 37° C. (100° F.) and atmospheric pressure. However, any temperature or pressure generally employed by those skilled in the art is within the scope of this invention.

The following examples serve to illustrate this invention without undue limitation of the scope thereof.

EXAMPLE I

This example describes a typical procedure used to prepare the alkali metal carboxyalkyl trithiocarbonates disclosed herein. To a one-Liter round-bottom flask equipped with a dropping funnel, condenser, stirrer and thermometer was charged 366 milliliters of water and 126 grams (3.15 moles) of sodium hydroxide. After the hydroxide had dissolved, 106.1 grams (1.0 mole) of 3-mercaptopropionic acid was slowly added with stirring. The addition was exothermic and was controlled below about 50° C. by means of an ice bath. After the addition was complete and the temperature had cooled below 40° C. there was slowly added with stirring 76.14 grams (1.0 mole) of carbon disulfide. After the addition, the thick yellow slurry was stirred 1 hour where upon 94.5 grams (1.0 mole) of chloroacetic acid dissolved in 100 milliliters of water was added to the stirred contents of the flask. This addition was also exothermic and had to be cooled below about 50° C. during the addition. After 2 to 3 hours stirring the reaction mixture was cooled to room temperature and bottled. The product at this point was assumed to be a 40 weight percent aqueous solution of mostly disodium 2-carboxyethylcarboxymethyl trithiocarbonate. Bis(sodium carboxymethyl)-trithiocarbonate was similarly prepared from aqueous sodium hydroxide, thioglycolic acid, $CS_2$, and chloroacetic acid.

EXAMPLE II

This example describes the evaluation of the products prepared in Example I as suppressants in a Mo ore flotation process. To a 3-Liter Agitar LA 500 flotation cell was added 400 milliliters (600 grams solids) of a Mo/-Cu/Fe-containing concentrate (69 percent solids available from Anamax Mines) along with enough water to raise the level a few inches below the lip of the cell. Added to the cell was the collector or suppressant to be evaluated. After conditioning for 1 to 2 minutes the slurry was floated for 5 minutes at 200 rpm and a natural pH of 10.4. In some experiments the pulp was acidified with $H_2SO_4$ and conditioned for 2 minutes before any reagent added. After floating, the concentrate was filtered, dried and analyzed. These results are listed in Table I where it can be seen that both of the inventive products suppressed Cu and Fe while continuing to allow Mo to float. The inventive products performed well over a broad pH range, the better Cu and Fe suppression and Mo recovery occurring under acid conditions. A similar but different product, disodium carboxymethyl trithiocarbonate—Run 3, performed well under basic conditions but also suppressed the desired Mo under acidic conditions. Molyflo, an oily Mo collector exhibited Cu and Fe suppression only at the lower pH 6.5.

TABLE I

Trithiocarbonate Salts as Suppressants in a Mo Ore Flotation Process (Anamax Concentrate)

| | | Wt. % Recovery | | | | | |
|---|---|---|---|---|---|---|---|
| | | pH 10.4 | | | pH 6.5 | | |
| Flotation Reagent | lb/T | Cu | Fe | Mo | Cu | Fe | Mo |
| Control: | | | | | | | |

TABLE I-continued

Trithiocarbonate Salts as
Suppressants in a Mo Ore Flotation Process
(Anamax Concentrate)

| | | Wt. % Recovery | | | | | |
|---|---|---|---|---|---|---|---|
| | | pH 10.4 | | | pH 6.5 | | |
| Flotation Reagent | lb/T | Cu | Fe | Mo | Cu | Fe | Mo |
| 1. None | — | 25.7 | 25.7 | 27.8 | 5.1 | 4.3 | 82.5 |
| 2. Molyflo[a] | .14 | 28.5 | 28.2 | 32.7 | 6.3 | 5.3 | 84.8 |
| 3. Na$_2$.Carboxymethyl Trithiocarbonate[b] | .8 | 3.4 | 4.0 | 57.9 | 3.0 | 4.0 | 6.3 |
| Invention: | | | | | | | |
| 4. Na$_2$.Bis(Carboxymethyl)-Trithiocarbonate[b] | .8 | 14.2 | 12.0 | 69.8 | 4.3 | 5.9 | 82.0 |
| 5. Na$_2$.Carboxymethyl 2-Carboxyethyl Trithiocarbonate[b] | .8 | 19.1 | 15.6 | 57.4 | 4.0 | 3.5 | 85.9 |

[a]An oily Mo collector from Phillips Petroleum Co.
[b]A 40 wt. % aqueous solution from Phillips Petroleum Co.

EXAMPLE III

This example describes the evaluation of one of the products prepared in Example I as a suppressant in a Mo ore flotation process using a different mineral source. About 400 milliliters of a Cu/Fe/Pb/Mo-containing concentrate (400 grams solids, available from Endako Mines) was added to a 1.6 Liter capacity Denver flotation cell along with 400 milliliters of water. The pH was about 8.4. The desired reagents were added and the pulp conditioned for 1 minute and floated for 2 minutes at 1200 rpm. The new concentrate was filtered, dried and analyzed. These results are listed in Table II where it can be seen that when disodium bis(carboxymethyl)-trithiocarbonate is used as a suppressant with a Mo ore concentrate the weight percent recovery of Cu, Fe and Pb is less (Runs 4a and 4b) than when a commercial suppressant like NaCN (Runs 2a and 2b) is used at near equal concentrations, the recovery of Mo remaining about 90 percent in both cases. In runs 3a and 3b another commercial suppressant was used as a control and again the inventive suppressant was significantly better for Cu and Fe suppression.

TABLE II

Effect of Bis(Carboxyalkyl)Trithiocarbonate
Salt as a Suppressant in a Mo Ore Flotation Process
(Endako Concentrate)

| | | Wt. % Recovery | | | |
|---|---|---|---|---|---|
| Flotation Reagent | lb/T | Cu | Fe | Pb | Mo |
| Control: | | | | | |
| 1. None | — | 39.7 | 15.6 | 44.4 | 89.2 |
| 2a. NaCN | 1.92 | 11.9 | 12.6 | 44.8 | 89.2 |
| 2b. NaCN | 3.84 | 7.4 | 12.0 | 44.2 | 89.3 |
| 3a. Na$_2$.Carboxymethyl Trithiocarbonate[a] | 0.76 | 28.9 | 16.2 | 45.8 | 88.9 |
| 3b. Na$_2$.Carboxymethyl Trithiocarbonate[a] | 1.54 | 10.9 | 13.6 | 29.7 | 90.1 |
| Invention: | | | | | |
| 4a. Na$_2$.Bis(Carboxymethyl) Trithiocarbonate | 0.76 | 21.4 | 15.9 | 29.7 | 89.1 |
| 4b. Na$_2$.Bis(Carboxymethyl) Trithiocarbonate | 1.54 | 8.0 | 12.0 | 44.2 | 88.9 |
| a. 40 Weight percent aqueous solution. | | | | | |

In summary, the data herein disclosed reveal that the novel dialkali metal bis(carboxyalkyl)-trithiocarbonate salts and diammonium bis(carboxyalkyl)-trithiocarbonate salts are useful as ore flotation agents. These compounds are particularly suited for suppressing copper and iron in the presence of molybdenum and/or lead in ore flotation processes.

Reasonable variations and modifications which will become apparent to those skilled in the art can be made in this invention without departing from the spirit and scope thereof.

We claim:

1. The composition represented by the formula

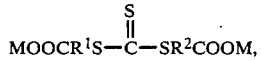

wherein M is selected from the group consisting of ammonium and alkali metals, $R^1$ is selected from the group consisting of alkylene radicals each radical having from 2 to 6 carbon atoms, $R^2$ is selected from the group consisting of alkylene radicals each radical having no more than 6 carbon atoms, and $R^1$ and $R^2$ are different.

2. A composition in accordance with claim 1 wherein $R^1$ is selected from the group consisting of linear alkylene radicals each radical having from 2 to 6 carbon atoms and branched alkylene radicals each radical having from 3 to 6 carbon atoms.

3. A composition in accordance with claim 2 wherein $R^2$ is selected from the group consisting of linear alkylene radicals each radical having from 1 to 6 carbon atoms and branched alkylene radicals each radical having from 3 to 6 carbon atoms.

4. A composition in accordance with claim 1 wherein M is sodium.

5. A composition in accordance with claim 4 wherein $R^1$ is an ethylene radical and $R^2$ is a methylene radical.

6. A composition in accordance with claim 1 wherein $R^1$ is an ethylene radical and $R^2$ is a methylene radical.

7. Disodium 2-carboxyethylcarboxymethyl trithiocarbonate.

8. A process for producing a composition having the formula

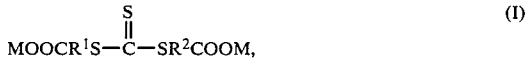

wherein M is selected from the group consisting of ammonium and alkali metals, $R^1$ is selected from the group consisting of alkylene radicals each radical having no more than 6 carbon atoms, $R^2$ is selected from the group consisting of alkylene radicals each radical having no more than 6 carbon atoms, and $R^1$ and $R^2$ can be the same or different, comprising the steps of:

(a) reacting a hydroxide having the formula $$MOH \qquad (II),$$

wherein M is selected from the group consisting of ammonium and alkali metals from Group IA of the Periodic Table of Elements, with a mercaptoalkanoic acid having the formula $$HOOCR^1-SH \qquad (III),$$

wherein $R^1$ is selected from the group consisting of alkylene radicals each radical having no more than 6 carbon atoms, and with $CS_2$ to form $$MOOCR^1S-\overset{\overset{S}{\|}}{C}-SM; \qquad (IV)$$

(b) reacting the product of formula (IV) with a haloalkanoic acid having the formula $$X-R^2COOH \qquad (V),$$

wherein X is selected from the group consisting of Cl, Br and I, and $R^2$ is selected from the group consisting of alkylene radicals each radical having no more than 6 carbon atoms, to form a composition having the formula (I); and (c) recovering said composition as the product of the process.

9. A process in accordance with claim 8 wherein X is Cl.

10. A process in accordance with claim 8 wherein M is sodium.

11. A process in accordance with claim 8 wherein $R^1$ is an ethylene radical and $R^2$ is a methylene radical.

12. A process in accordance with claim 11 wherein M is sodium.

13. A process in accordance with claim 8 wherein $R^1$ is a methylene radical and $R^2$ is a methylene radical.

14. A process in accordance with claim 13 wherein M is sodium.

15. A process for recovering minerals comprising:
(a) mixing crushed ore containing minerals, water and a composition having the formula $$MOOCR^1S-\overset{\overset{S}{\|}}{C}-SR^2COOM,$$

wherein M is selected from the group consisting of ammonium and alkali metals, $R^1$ is selected from the group consisting of alkylene radicals each radical having no more than 6 carbon atoms, $R^2$ is selected from the group consisting of alkylene radicals each radical having no more than 6 carbon atoms, and $R^1$ and $R^2$ can be the same or different, to establish a pulp;

(b) aerating said thus established pulp to produce a froth containing said minerals; and (c) recovering said minerals from said thus produced froth.

16. A process in accordance with claim 15 wherein $R^1$ and $R^2$ are each selected from the group consisting of linear alkylene radicals each radical having from 1 to 6 carbon atoms and branched alkylene radicals each radical having from 3 to 6 carbon atoms.

17. A process in accordance with claim 15 wherein M is sodium, $R^1$ is an ethylene radical and $R^2$ is a methylene radical.

18. A process in accordance with claim 15 wherein M is sodium, $R^1$ is a methylene radical and $R^2$ is a methylene radical.

19. A process for recovering minerals comprising:
(a) mixing crushed ore containing said minerals, water and a composition produced in accordance with the process of claim 8 to establish a pulp;
(b) aerating said thus established pulp to produce a froth containing at least a portion of said minerals; and
(c) recovering said minerals from said thus produced froth.

20. A process in accordance with claim 19 wherein said ore comprises Mo, Cu and Fe, and said composition suppresses Cu and Fe from said froth to enhance the selective recovery of Mo from said froth.

21. A process for recovering minerals comprising:
(a) mixing a rougher concentrate containing said minerals, water and a composition produced in accordance with the process of claim 8 to establish a pulp;
(b) aerating the thus established pulp to produce a froth containing at least a portion of said minerals; and
(c) recovering said minerals from said thus produced froth.

22. A process in accordance with claim 21 wherein said ore comprises Mo, Cu and Fe, and said composition suppresses Cu and Fe from said froth to enhance the selective recovery of Mo from said froth.

* * * * *